(12) United States Patent
Fukuta et al.

(10) Patent No.: US 7,734,339 B2
(45) Date of Patent: Jun. 8, 2010

(54) IONTOPHORESIS APPARATUS

(75) Inventors: Kenji Fukuta, Shunan (JP); Kanji Sakata, Shunan (JP)

(73) Assignee: Tokuyama Corporation, Shunan-shi (JP)

( * ) Notice: Subject to any disclaimer, the term of this patent is extended or adjusted under 35 U.S.C. 154(b) by 852 days.

(21) Appl. No.: 10/536,398

(22) PCT Filed: Nov. 26, 2003

(86) PCT No.: PCT/JP03/15105

§ 371 (c)(1),
(2), (4) Date: Jan. 3, 2006

(87) PCT Pub. No.: WO2004/047916

PCT Pub. Date: Jun. 10, 2004

(65) Prior Publication Data

US 2006/0241548 A1   Oct. 26, 2006

(30) Foreign Application Priority Data

Nov. 27, 2002   (JP) ............................. 2002-343158

(51) Int. Cl.
*A61N 1/30* (2006.01)
(52) U.S. Cl. .................................... 604/20; 424/443
(58) Field of Classification Search ............ 604/20; 424/443
See application file for complete search history.

(56) References Cited

U.S. PATENT DOCUMENTS

| 5,246,417 | A | * | 9/1993 | Haak et al. ............. 604/20 |
| 5,503,632 | A | * | 4/1996 | Haak ...................... 604/20 |
| 5,941,843 | A | | 8/1999 | Atanasoska et al. |
| RE37,307 | E | * | 8/2001 | Bahar et al. ........... 204/296 |
| 2001/0018568 | A1 | * | 8/2001 | Iga et al. ................ 604/20 |
| 2002/0134687 | A1 | | 9/2002 | Nakajima et al. |

FOREIGN PATENT DOCUMENTS

| JP | 63-99246 A | 4/1988 |
| JP | 3-40517 A | 2/1991 |
| JP | 03094771 A | 4/1991 |
| JP | 3-504343 A | 9/1991 |
| JP | 4-297277 A | 10/1992 |
| JP | 042997277 A | 10/1992 |
| JP | 6-503258 A | 4/1994 |
| JP | 9-108362 A | 4/1997 |
| JP | 9-201420 A | 8/1997 |

(Continued)

*Primary Examiner*—Nicholas D Lucchesi
*Assistant Examiner*—Laura A Bouchelle
(74) *Attorney, Agent, or Firm*—Birch, Stewart, Kolasch & Birch, LLP

(57) ABSTRACT

An iontophoresis device comprising (A) a working electrode assembly having a working electrode, a medicine-containing portion and an ion-exchange membrane, (B) a counter electrode assembly having an electrode which opposes the working electrode, and (C) a power source unit electrically connected to the working electrode assembly and to the counter electrode assembly, enabling an ionic medicine contained in the medicine containing portion to be permeated into a living body by the electrophoresis through the ion-exchange membrane, wherein the ion-exchange membrane has a structure in which voids of a porous film are filled with an ion-exchange resin. The iontophoresis device using the above ion-exchange membrane makes it possible to administer the medicine in amounts larger than those accomplished by using the conventional devices.

4 Claims, 2 Drawing Sheets

FOREIGN PATENT DOCUMENTS

| | | |
|---|---|---|
| JP | 09212964 A | 8/1997 |
| JP | 11-239621 A | 9/1999 |
| JP | 2000229128 A | 8/2000 |
| JP | 2002338721 A | 11/2002 |
| WO | WO 90/04433 A1 | 5/1990 |
| WO | WO-92/07649 A1 | 5/1992 |
| WO | WO-97/12644 A1 | 4/1997 |
| WO | WO 9712644 A1 * | 4/1997 |

* cited by examiner

IONTOPHORESIS APPARATUS

FIELD OF THE INVENTION

The present invention relates to an iontophoresis device for carrying out the iontophoresis (ionic permeation therapy) for permeating, into the living body, an ionic medicine useful for the living body by utilizing the electrophoresis. More specifically, the invention relates to an iontophoresis device which uses an ion-exchange membrane and to an ion-exchange membrane used for the above device.

BACKGROUND ART

The iontophoresis for permeating, into the living body, an ionic medicine useful for the living body by utilizing the electrophoresis has also been called ionic permeation therapy or ion introduction method, and has been widely known as a method of administering a medicine of a required amount into a diseased part in a pain-free state.

In the iontophoresis, so far, a medicine-containing layer impregnated with an ionic medicine is placed on the living body, a working electrode is arranged on the side opposite to the living body with the medicine layer sandwiched therebetween, a counter electrode is placed on the living body separated away from the medicine-containing layer, and an electric current is permitted to flow across the working electrode and the counter electrode from a power source causing the ionic medicine to permeate into the living body. This method has an object of permeating the ionic medicine only into the living body through the living body interface such as the skin and the mucous membrane. According to this method, however, the ionic medicine does not necessarily pass through the living body interface but, conversely, it often happens that sodium cations, potassium cations and chloride anions permeate back into the medicine layer from the side of the living body. In particular, ionic medicines that are believed to be useful for the living body have a smaller mobility than those of ions existing in the living body, and a desired medicine is not efficiently administered (does not efficiently permeate into the living body) in proportion to the time the electricity is supplied. In the iontophoresis, further, the medicine comes into direct contact with the electrodes triggering a reaction on the electrodes not only wasting the medicine but also forming compounds that may adversely affect the living body. Moreover, the medicine is usually used in the form of an aqueous solution. Therefore, the electrolysis of water takes place on the working electrode and on the counter electrode, whereby the pH of the medicine-containing aqueous solution varies due to $H^+$ ions and $OH^-$ ions that are formed often causing the living body to be inflamed.

In order to solve these problems, new iontophoretic methods have been proposed by arranging an ion-exchange membrane on the living body interface so that ionic medicine permeates into the living body through the ion-exchange membrane (e.g., see patent documents 1 to 4).

[Patent document 1] JP-A-3-94771

[Patent document 2] JP-T-3-504343

[Patent document 3] JP-A-4-297277

[Patent document 4] JP-A-2000-229128

According to the systems proposed in the above patent documents, the ion-exchange membrane arranged on the living body interface permits the permeation of only those ions having the same charge as the desired medicine ions. This makes it possible to prevent the ions having a charge opposite to that of the desired medicine from oozing out of the living body and, hence, to accomplish a high dosage of the medicine as compared with when no ion-exchange membrane is arranged. The above technologies use a commercial ion-exchange membrane which employs, as a reinforcing member (reinforcement), a woven fabric, that is used for the manufacture of the salt and for the dialysis of food compounds.

So far, the iontophoresis has used a large device and could be practiced in particular places only such as in a hospital. In order to realize the iontophoresis at any time in any place, therefore, study has been forwarded vigorously concerning the iontophoresis devices that feature simple and compact structures and that can be carried.

The iontophoresis device of the portable type usually uses cells such as button-type cells as a power source. Therefore, the dosage of the medicine becomes particularly important when the voltage remains constant (constant voltage) rather than when the current remains constant (constant current).

Further, the administration of medicine by the iontophoresis and, particularly, the administration of medicine by using a portable iontophoresis device is continued over a relatively long period of time unlike that of the method such as the injection. It is therefore desired that the patient is allowed to move around and behave while carrying the iontophoresis device.

However, even the above iontophoresis method using the ion-exchange membrane is not satisfactory concerning the dosage of the medicine and, particularly, the dosage of the medicine in a constant-voltage state, and it has been desired to accomplish a further improved dosage.

Further, if the patient behaves while carrying the iontophoresis device, the portions of the skin to where the iontophoresis device is fitted are expanded, contracted and bent. Therefore, the ion-exchange membrane used for the iontophoresis device must be so strong as will not be broken by the stress generated by the expansion, contraction and bending. In general, the membrane exhibits a strength that increases with an increase in the thickness thereof. However, an increase in the thickness of the membrane, at the same time, causes a decrease in the flexibility and, hence, a decrease in the follow-up property for the expansion, contraction and bending. Therefore, if an ion-exchange membrane having a large thickness is used by giving importance to the strength, then, such problems arouse that the iontophoresis device peels off the skin or is disconnected while being carried.

SUMMARY OF THE INVENTION

It is, therefore, an object of the present invention to provide an iontophoresis device which can be suitably used as the one of the portable type in the iontophoresis by using an ion-exchange membrane, featuring a large dosage of the desired medicine, and enabling the patient to behave while carrying the iontophoresis device without causing the iontophoresis device to be broken or disconnected.

Another object of the present invention is to provide an ion-exchange membrane used for the above iontophoresis device.

The present inventors have conducted extensive study to solve the above problems. As a result, the inventors have discovered that the dosage of the medicine is greatly enhanced under a constant-voltage condition by using an ion-exchange membrane that employs a porous film as a reinforcement. The inventors have further discovered that the ion-exchange membrane using the porous film as the reinforcement is very thinner and more flexible than the ion-exchange membranes that use the conventional woven fabric, yet exhibiting excellent strength, and have finished the present invention.

That is, according to the present invention, there is provided an iontophoresis device comprising (A) a working electrode assembly having a working electrode, a medicine-containing portion and an ion-exchange membrane, (B) a counter electrode assembly having an electrode which opposes the working electrode, and (C) a power source unit electrically connected to the working electrode assembly and to the counter electrode assembly, enabling an ionic medicine contained in the medicine containing portion to be permeated into a living body by the electrophoresis through the ion-exchange membrane, wherein the ion-exchange membrane has a structure in which voids of a porous film are filled with an ion-exchange resin.

According to the present invention, there is further provided a working electrode assembly for the iontophoresis including an electrode, an ionic medicine-containing layer and an ion-exchange membrane arranged in this order, wherein the ion-exchange membrane has a structure in which voids of a porous film are filled with an ion-exchange resin.

According to the present invention, there is further provided an ion-exchange membrane for the iontophoresis having a structure in which voids of a porous film are filled with an ion-exchange resin.

BEST MODE FOR CARRYING OUT THE INVENTION

Figure 1:
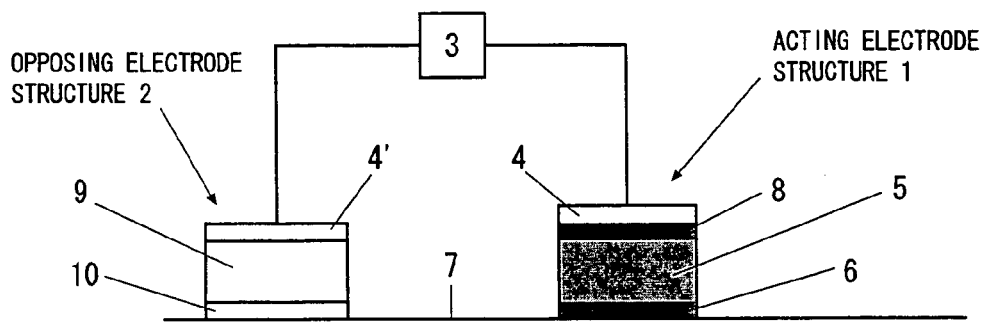
FIG. 1 is a view schematically illustrating a representative constitution of an iontophoresis device of the present invention.

The iontophoresis device of the present invention is used for administering an ionic medicine into a living body by utilizing the electrophoresis, and has a feature on the use of an ion-exchange membrane that employs a porous film as a reinforcement, and administers the ionic medicine into the living body through the ion-exchange membrane. As shown in FIG. 1, the iontophoresis device is constituted by a working electrode assembly 1, a counter electrode assembly 2, and a power source unit 3 electrically connected to these structures.

(Working Electrode Assembly 1)

The working electrode assembly 1 includes an electrode (working electrode) 4 that serves as a working electrode, a medicine-containing portion 5 containing an ionic medicine, and an ion-exchange membrane 6 using a porous film as the reinforcement. The ion-exchange membrane 6 selectively permits the permeation of ions of the same polarity as the pharmacological ions of the ionic medicine to be administered. In the working electrode assembly 1 as shown in FIG. 1, there are arranged the working electrode 4, medicine-containing portion 5 and ion-exchange membrane 6 in this order. Usually, these members are laminated in an backing material (not shown) to constitute the working electrode assembly 1, and the ion-exchange membrane 6 is arranged to be positioned on a living body interface (skin).

An ion-exchange membrane 8 may further be included between the electrode and the medicine-containing layer to prevent the decomposition of the medicine to be administered and to prevent the pH of the medicine-containing portion 5 from being varied by the electrode reaction. It is desired that the ion-exchange membrane 8 is the one which selectively permits the passage of ions of a polarity opposite to that of the pharmacological ions.

As required, further, an ion-permeating sheet made of an ionically conducting gel, a porous film or a woven fabric may be provided between the ion-exchange membrane 6 and the living body interface. The gel or the sheet may assume a structure integral with the working electrode assembly 1. Or, the gel or the sheet may be held relative to the living body interface only during the use. Though not illustrated, the working electrode assembly 1 may further include an ionically conducting gel, an ionically electrolytic solution, or a porous film or a woven fabric impregnated with the ionically electrolytic solution between the working electrode 4 and the ion-exchange membrane 8.

As the working electrode 4 in the working electrode assembly 1, there can be used, without limitation, any electrode that is usually used in the electrochemical processes. For example, there can be used an electrode made of an electronically conducting material such as gold, platinum, silver, copper, nickel, zinc or carbon, or a self-sacrificing electrode such as semiconductor electrode or silver/silver chloride, which may be used alone or in combination. Preferably, there can be exemplified gold, platinum, silver and carbon. These electrodes may be plates, sheets, meshes or an amorphous laminate of fibers, which is shaped and worked like a paper, or may be the one obtained by plating or vaporizing an electrode member on an ion-exchange membrane.

As the medicine-containing portion 5 in the working electrode assembly 1, there can be used, without any limitation, a medicine-containing layer that is used in the ordinary iontophoresis. That is, there can be used a solution obtained by dissolving an ionic medicine in a solvent such as water or ethanol, a gel obtained by mixing the above solution with a polyvinyl alcohol or a polyvinyl pyrrolidone, or the one obtained by impregnating a porous film or a gauze with the above solution. There is no particular limitation on the ionic medicine contained in the medicine-containing portion 5. The ionic medicine may be any substance that comprises cations and anions and exhibits pharmacological effect as the positive ions or negative ions enter into the living body.

Examples of the ionic medicine of which the positive ions exhibit the effect include anesthetics such as procaine hydrochloride, lidocaine hydrochloride and dibucaine hydrochloride; anti-malignant tumor agents such as mitomycin and pleomycin hydrochloride; anodynes such as morphine hydrochloride; steroids such as medroxyprogesterone acetate; histamine and insulin. As the ionic medicine of which the negative ions exhibit the effect, there can be exemplified vitamin compounds such as vitamin B2, vitamin B12, vitamin C, vitamin E and folic acid; anti-inflammatory agents such as aspirin and ibuprofen; adrenocortical hormones such as dexamethasone-type water-soluble compounds; and antibiotics such as benzylpenicillin potassium.

—Ion-Exchange Membrane 6—

In the present invention, the ion-exchange membrane 6 using a porous film as the reinforcement has an ion-exchange resin with a cation exchanging function or an anion exchanging function filled in part or whole of the voids of the porous film.

The ion-exchange resin may be a fluorinated ion-exchange resin having ion-exchange groups introduced into the perfluorocarbon skeleton, or a so-called hydrocarbon-type ion-exchange resin having a skeleton of a resin that has not been fluorinated. From the simplicity of the production steps, however, it is desired that the ion-exchange resin is the one of the hydrocarbon type. The ratio of the ion-exchange resin filled in the ion-exchange membrane 6 is usually 5 to 95% by weight, and is, preferably, 10 to 90% by weight to facilitate the permeation of the pharmacological ions and to increase the strength of the ion-exchange membrane and is, particularly preferably, 20 to 60% by weight though it may vary depending upon the percentage of voids of the porous film that will be described later.

There is no particular limitation on the ion-exchange group present in the ion-exchange resin provided it is a functional group capable of forming a group having a negative or positive electric charge in an aqueous solution. As the functional group that could become the ion-exchange group, there can be exemplified sulfonic acid group, carboxylic acid group and phosphonic acid group, which are the cation-exchange groups. These acid groups may exist in the form of free acids or salts. As the pair cations of the case of salts, there can be exemplified alkali metal cations such as sodium ions and potassium ions, or ammonium ions. Among these cation-exchange groups, it is generally desired to use a sulfonic acid group which is a strongly acidic group. As the anion-exchange group, there can be exemplified primary to tertiary amino groups, quaternary ammonium group, pyridyl group, imidazole group, quaternary pyridinium group and quaternary imidazolium group. As the pair anions in these anion-exchange groups, there can be exemplified halogen ions such as chlorine ions and hydroxy ions. Among these anion-exchange groups, there is usually used the quaternary ammonium group or the quaternary pyridinium group which is a strongly basic group.

It is desired that the ion-exchange resin is of the crosslinked type from the standpoint of excellent strength and excellent stability against various solvents.

The ion-exchange membrane 6 used in the present invention has the greatest feature in that the above ion-exchange resin is formed as a membrane using a porous film as the reinforcement. The ion-exchange membrane using the customarily employed woven fabric as the reinforcement fails to possess both sufficiently large strength and flexibility, and exhibits a low medicine administering efficiency. Further, even the ion-exchange membrane of the cast type formed without using the reinforcement cannot satisfy both sufficiently large strength and flexibility. Besides, the ion-exchange membrane of the cast type dissolves in, or swells with, the solvent contained in the medicine-containing layer, and is not capable of forming the iontophoresis device which is substantially utilizable.

In the present invention, as the porous film used as the reinforcement for the ion-exchange membrane, there can be used, without any limitation, the one which is in the form of a film or a sheet having many pores penetrating through from the front surface to the back surface. To obtain both a large strength and flexibility, it is desired to use the porous film made of a thermoplastic resin.

As the thermoplastic resin that constitutes the porous film, there can be used without limitation polyolefin resins such as homopolymers or copolymers of α-olefins like ethylene, propylene, 1-butene, 1-pentene, 1-hexene, 3-methyl-1-butene, 4-methyl-1-pentene, and 5-methyl-1-heptene; vinyl chloride resins such as polyvinyl chloride, vinyl chloride/vinyl acetate copolymer, vinyl chloride/vinylidene chloride copolymer, and vinyl chloride/olefin copolymer; fluorine-contained resins such as polytetrafluoroethylene, polychlorotrifluoroethylene, vinylidene polyfluoride, tetrafluoroethylene/hexafluoropropylene copolymer, tetrafluoroethylene/perfluoroalkylvinyl ether copolymer and tetrafluoroethylene/ethylene copolymer; polyamides such as nylon 6 and nylon 66; and polyimide resin. It is, however, desired to use a polyolefin resin from the standpoint of mechanical strength, flexibility, chemical stability, resistance against the chemicals, and compatibility with the ion-exchange resin. As the polyolefin resin, it is particularly preferred to use a polyethylene and a polypropylene, and it is most desired to use the polyethylene.

There is no particular limitation on the property of the porous film made of the above thermoplastic resin. From the standpoint of obtaining an ion-exchange membrane having a small thickness, a large strength and a low electric resistance, however, it is desired that the pores have an average diameter of, preferably, 0.005 to 5.0 µm, more preferably, 0.01 to 2.0 µm and, most preferably, 0.02 to 0.2 µm. The above average porous diameter stands for an average diameter measured in compliance with the Bubble Point Method (JIS K 3832-1990). Similarly, it is desired that the percentage of voids is, preferably, 20 to 95% and, more preferably, 30 to 90% and, most preferably, 30 to 60%. Further, the thickness of the porous film is, preferably, 5 to 140 µm, more preferably, 10 to 120 µm and, most preferably, 15 to 55 µm so that the ion-exchange membrane will assume the thickness as will be described later. The ion-exchange membrane produced by the production method that will be described later, usually, has a thickness equal to about the thickness of the porous film used as the reinforcement plus 0 to 20 µm.

The porous film can be obtained according to the methods taught in JP-A-9-235399 and JP-A-2002-338721. Concretely speaking, the porous film is prepared by mixing an organic liquid to a thermoplastic resin to mold it into sheet or a film and, then, extracting the organic liquid from the obtained sheet or film by using a solvent. The porous film can be further prepared even by stretching a film of a resin composition obtained by blending the thermoplastic resin with an inorganic filler and/or an organic filler. The porous film is further available in the market in the names of, for example "Hipore" manufactured by Asahi Kasei Co., "U-Pore" manufactured by Ube Kosan Co., "Setela" manufactured by Tonen Talpis Co., "Expole" manufactured by Nitto Denko Co., "Hilet" manufactured by Mitsui Chemicals Inc., etc.

In the present invention, it is desired that the ion-exchange membrane 6 using the above porous film as the reinforcement has an amount of the ion-exchange group of 0.1 to 6.0 mmols/g, and, particularly, 0.3 to 4.0 mmols/g as the ion-exchange capacity. As the ion-exchange capacity increases, the electric resistance of the ion-exchange membrane decreases and the medicine can be administered in an increased amount at a constant voltage. If the ion-exchange capacity exceeds 4.0 mmols/g, however, the production thereof becomes difficult. If 6.0 mmols/g is exceeded, the production becomes substantially impossible.

It is further desired that the ion-exchange membrane 6 has a water content of not smaller than 5% and, preferably, not smaller than 10% so that its electric resistance will not increase due to drying. Usually, the water content is maintained to be about 5 to 90%. The water content can be maintained in this range by selecting the kind of the ion-exchange groups and by controlling the ion-exchange capacity and the degree of crosslinking. To administer the desired medicine in large amounts, further, it is desired that the ion-exchange membrane 6 has a fixed ion concentration of 6.0 to 15.0 mmols/g of water.

It is further desired that the ion-exchange membrane 6 has a thickness of, preferably, 5 to 150 µm, more preferably, 10 to 130 µm, and, particularly preferably, 15 to 60 µm. When the thickness is large, the ion-exchange membrane 6 exhibits an increased strength. When the thickness is small, on the other hand, the ion-exchange membrane 6 exhibits excellent follow-up property to the surface of the living body and a decreased electric resistance. To realize the iontophoresis device of the present invention in a portable form, it is desired that the ion-exchange membrane 6 has a strength of not smaller than 0.1 MPa and, particularly, not smaller than 0.2 MPa as the burst strength, and has a flexibility of not larger than 15 $cm^3$/100, particularly, not larger than 10 $cm^3$/100 and, most particularly, not larger than 5 $cm^3$/100 as the Clark's stiffness degree.

When the iontophoresis device of the present invention is used in a manner that the ion-exchange membrane 6 comes into direct contact with the surface of the living body such as the skin, it is desired that the ion-exchange membrane 6 has a smooth surface from the standpoint of accomplishing intimate contact to the surface of the living body. For instance, it is desired that the ion-exchange membrane 6 has a 10-point height of roughness profile Rz (JIS B 0601-1994) of not larger than 10 µm and, preferably, not larger than 5 µm. The ion-exchange membrane 6 having the smooth surface yet featuring excellent strength and flexibility is obtained for the first time by using a porous film as the reinforcement but is not obtained when a conventional woven fabric or the like is used as the reinforcement.

There is no particular limitation on the method of producing the ion-exchange membrane 6 used in the present invention provided the above-mentioned porous film is used as the reinforcement. Particularly preferably, however, the ion-exchange membrane 6 is produced by a method described below from the standpoint of efficiently producing a film of high performance.

Namely, a monomer composition comprising a monomer having a functional group capable of introducing an ion-exchange group, a crosslinking monomer and a polymerization initiator, is filled in the voids in the porous film, and is polymerized so that the cation-exchange groups or the anion-exchange groups are introduced into the polymer.

In this production method, a hydrocarbon monomer that has heretofore been used in the production of a known ion-exchange resin can be used without any limitation as the monomer having a functional group capable of introducing an ion-exchange group.

As the hydrocarbon monomer having a functional group capable of introducing a cation-exchange group, there can be exemplified aromatic vinyl compounds such as styrene, α-methylstyrene, 3-methylstyrene, 4-methylstyrene, 2,4-dimethylstyrene, p-tert-butylstyrene, α-halogenated styrene and vinylnaphthalene, which may be used in one kind or in two or more kinds.

As the monomer having a functional group capable of introducing an anion-exchange group, on the other hand, there can be exemplified styrene, vinyltoluene, chloromethylstyrene, vinylpyridine, vinylimidazole, α-methylstyrene and vinylnaphthalene.

As the crosslinking monomer, though there is no particular limitation, there can be used polyfunctional vinyl compounds such as divinylbenzenes, divinylsulfone, butadiene, chloroprene, divinylbiphenyl and trivinylbenzene, as well as polyfunctional methacrylic acid derivatives such as trimethylolmethanetrimethacrylic acid ester, methylenebisacrylamide and hexamethylenedimethacrylamide.

As required, further, there may be added other hydrocarbon monomers copolymerizable with the above monomers or crosslinking monomers and plasticizers in addition to the above-mentioned components. As the other monomers, there can be used, for example, acrylonitrile, acrolein and methyl vinyl ketone. As the plasticizers, further, there can be used dibutyl phthalate, dioctyl phthalate, dimethyl isophthalate, dibutyl adipate, triethyl citrate, acetyltributyl citrate, dibutyl sebacate and dibenzyl ether.

As the polymerization initiator, there can be used any known one without limitation. Concrete examples of the polymerization initiator include organic peroxides such as octanoyl peroxide, lauroyl peroxide, t-butylperoxy-2-ethyl hexanoate, benzoyl peroxide, t-butylperoxyisobutylate, t-butylperoxylaurate, t-hexylperoxybenzoate, and di-t-butyl peroxide.

There may be further blended known additives used for the preparation of ion-exchange membranes.

In the above monomer composition, it is desired that the crosslinking monomer is blended in an amount of 0.1 to 50 parts by mass and, preferably, 1 to 40-parts by mass per 100 parts by mass of the monomer having a functional group capable of introducing the ion-exchange group, and that other monomers copolymerizable with the above monomers are used in amounts of 0 to 100 parts by mass. The obtained ion-exchange membrane exhibits an excellent strength when the amount of the crosslinking monomer is great though it may vary depending upon the kind of the crosslinking monomer. When the amount of the crosslinking monomer is too large, however, the flexibility decreases and the ion-exchange membrane tends to exhibit an increased electric resistance. It is further desired that the polymerization initiator is blended in an amount of 0.1 to 20 parts by mass and, preferably, 0.5 to 10 parts by mass per a total of 100 parts by mass of the crosslinking monomer and the monomer having a functional group capable of introducing the ion-exchange group.

The monomer composition comprising the above monomer having a functional group capable of introducing the ion-exchange group, the crosslinking monomer, the polymerization initiator and other blended components, is filled in the porous film and is polymerized. There is no particular limitation on the method of filling the above monomer composition in the porous film. For example, the monomer composition is applied or sprayed onto the porous film. Or, the porous film is immersed in the monomer composition. In applying the monomer composition, the two may be brought into contact with each other under a reduced pressure or may be pressurized after they have been contacted to each other, so that the voids in the porous film are favorably filled with the monomer composition. Further, the monomer composition filled in the porous film is polymerized preferably by a method of holding the porous film by films such as of a polyester having smooth surfaces while exerting the pressure and elevating the temperature starting from the normal temperature. Polymerization upon being held by the films is not hampered by oxygen in the environment and smooth surfaces as described above are obtained after the polymerization. The polymerization conditions may be suitably determined depending upon the kind of the polymerization initiator and the monomer composition that are used. Usually, a state heated at about 80 to 120° C. is maintained for about 5 minutes to about 10 hours.

Thereafter, the polymer filled in the porous film is put to a known treatment for introducing the ion-exchange groups to obtain an ion-exchange membrane. A known method may be suitably selected for introducing the ion-exchange groups. To obtain a cation-exchange membrane, for example, there may be conducted a processing such as sulfonation, chlorosulfonation, phosphonium-imparting treatment or hydrolysis. To obtain an anion-exchange membrane, there may be conducted a processing such as amination or alkylation.

There is no problem even when the ion-exchange membrane used in the present invention is produced by a known method of producing the ion-exchange membrane other than the above method. For example, the ion-exchange membrane can further be obtained by using a hydrocarbon type monomer having a cation-exchange group, such as a sulfonic acid type monomer such as of styrenesulfonic acid, vinylsulfonic acid or α-halogenated vinylsulfonic acid, a carboxylic acid type monomer such as of methacrylic acid, acrylic acid or anhydrous maleic acid, a phosphonic acid type monomer such as of vinylphosphoric acid, salts thereof, or a monomer having an anion-exchange group, such as an amine type monomer such as vinylbenzyltrimethylamine, vinylbenzyltriethylamine or trimethylaminoethyl methacrylate, a nitrogen-containing heterocyclic monomer such as vinylpyridine or vinylimidazole, salts thereof or esters thereof, i.e., by using a monomer composition comprising thereof, a crosslinking monomer, a polymerization initiator and other components, and filling the monomer composition in the porous film followed by the polymerization.

Further, instead of using the above monomer composition, an ion-exchange resin soluble in a solvent may be mixed with the solvent, or a resin having a functional group capable of introducing an ion-exchange group may be mixed with the solvent, to obtain a solution thereof or a paste-like composition thereof. The porous film is impregnated with the above solution or the paste-like composition and, thereafter, the solvent is removed. When an ion-exchange resin is used, the ion-exchange membrane is obtained by removing the solvent therefrom. When there is used a resin having a functional group capable of introducing the ion-exchange group, the ion-exchange group may be introduced by a known method after the solvent has been removed.

(Counter Electrode Assembly 2)

The counter electrode assembly 2 has an electrode (counter electrode) 4' that opposes the working electrode 4 of the working electrode assembly 1 and can assume, without any limitation, a structure used for a portion including an electrode that becomes a counter electrode in an ordinary iontophoresis device. That is, the counter electrode assembly 2 may be the electrode (counter electrode 4') itself, may be a structure in which the electrode (counter electrode 4') is arranged on a sheet of an ionically conducting gel, a porous film or a woven fabric, or may be a structure in which the electrode (counter electrode 4') is arranged on an ion-exchange membrane using a porous film as the reinforcement or on any other ion-exchange membrane. Preferably as shown in FIG. 1, the counter electrode 4', an electrolyte-containing portion 9 containing an ionic electrolyte and an ion-exchange membrane 10 are laminated in this order, the ion-exchange membrane 10 being arranged on the living body interface. In this case, the ion-exchange membrane 10 may be the one using the above porous film as the reinforcement or may be any other one. The ion-exchange membrane 10 may be the one which selectively permits the permeation of ions of a polarity same as, or opposite to, that of the pharmacological ions of the desired medicine. Preferably, however, the ion-exchange membrane 10 is the one that selectively permeates ions of the polarity opposite to that of the pharmacological ions of the desired medicine to prevent the permeation of the desired medicine into the counter electrode assembly from the living body.

The electrolyte-containing portion 9 in the counter electrode assembly 2 may be a solution itself obtained by dissolving an ionic electrolyte in a solvent such as water or an ethanol, a gel obtained by mixing the above solution with a polyvinyl alcohol or a polyvinyl pyrrolidone, or the one obtained by impregnating a porous film or a gauze with the above solution. There can be used any ionic electrolyte without limitation, such as sodium chloride or potassium chloride, if it dissolves in a solvent such as water or ethanol and exhibits ionic property.

Further, like in the case of the working electrode assembly 1, the counter electrode assembly 2 may be provided with an ion-exchange membrane between the counter electrode 4' and the ion-exchange membrane 10, may be provided with a sheet capable of permeating ions comprising an ionically conducting gel, a porous film or a woven fabric between the ion-exchange membrane 10 and the living body interface, or may be provided with an ionically conducting gel or an ionically electrolytic solution or with a porous film or a woven fabric impregnated with the ionically electrolytic solution between the counter electrode 4' and the ion-exchange membrane closest thereto.

(Power Source Unit 3)

As the power source unit 3 in the iontophoresis device of the present invention, there can be used any power source unit that is used in an ordinary iontophoresis device without limitation. When the working electrode assembly 1, counter electrode assembly 2 and the power source unit 3 are independent from each other, there can be used an external power source that can be connected to a battery or to a power source of the system. In such a case, it is desired to use in combination a power source control system such as a system for stabilizing the voltage or the current or a system for applying a pulse current.

Figure 3:
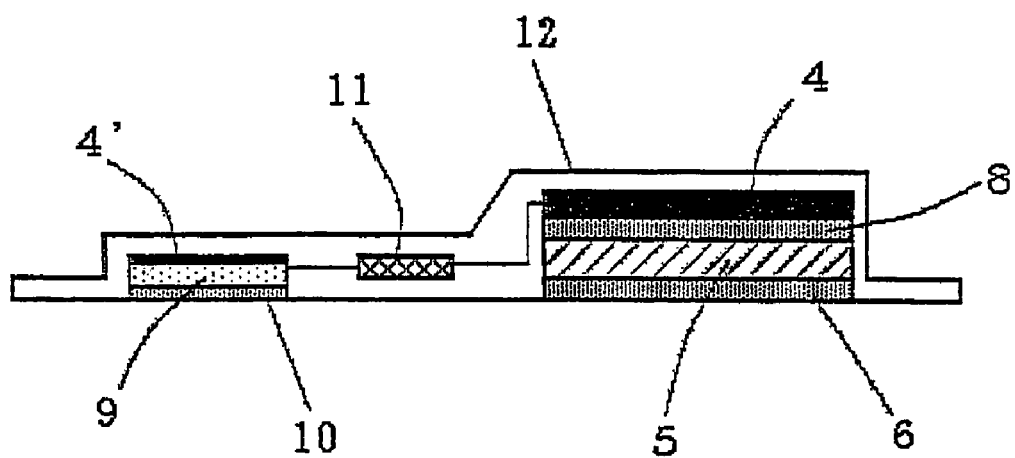
FIG. 3 is a sectional view schematically illustrating a portable iontophoresis device in which all constituent members are incorporated in a backing material.

When the iontophoresis device of the present invention is to be realized in a portable form, it is desired to use a cell as the power source. As the cell, there can be exemplified a coin type silver oxide cell, an air-zinc cell or a lithium ion cell. By using the above small cell as a power source, there can be obtained an iontophoresis device as shown in FIG. 3, which is small in size and easy to carry incorporating the working electrode assembly 1, the counter electrode assembly 2 and the power source unit 3 in a backing material. In fabricating the portable iontophoresis device, it is desired that the backing material is a highly flexible resin or rubber to realize a high follow-up property to the skin shape.

There is no particular limitation on the use of the iontohoresis device of the present invention. Namely, the iontophoresis device may be used in a customary manner, usually, by bringing the working electrode assembly 1 and the counter electrode assembly 2 into intimate contact with the surface of the living body which is the object to where the medicine is to be permeated, and by flowing a current by applying a voltage from the power source unit 3. In this case, the ion-exchange membrane 6 in the working electrode assembly 1 is so disposed as to be positioned between the medicine-containing portion 5 and the surface of the living body, so that the ions having a pharmacological effect produced from the ionic medicine in the medicine-containing portion 5 permeate into the living body passing through the ion-exchange membrane 6.

The iontophoresis device of the present invention using the ion-exchange membrane 6 employing the porous film as the reinforcement makes it possible to administer the desired medicine in very large amounts in addition to obtaining various effects of the conventional iontophoresis device that uses the ion-exchange membrane. Owing to its large amount of administration, the iontophoresis device of the invention can be realized in a small size with ease. Namely, there is particularly effectively realized a portable iontophoresis device which is not peeled off and which does not permit the ion-exchange membrane to be broken even if a person carrying it moves around.

EXAMPLES

The invention will be described more concretely by way of the following Examples and Comparative Examples to which only, however, the invention is in no way limited. Properties of the ion-exchange membranes shown in Examples and Comparative Examples were measured by the methods described below.

(1) Ion-Exchange Capacity and Water Content:

The ion-exchange membrane was immersed in a 1 (mol/l) HCl aqueous solution for not less than 10 hours.

Thereafter, in the case of the cation-exchange membrane, the proton type was changed to the sodium ion type with a 1 (mol/l) NaCl aqueous solution, and the liberated proton were titrated with a sodium hydroxide aqueous solution by using a potential-difference titration device (COMTITE-900, manufactured by Hiranuma Sangyo Co.)(A mols). In the case of the anion-exchange membrane, on the other hand, a chloride ion type exchange resin was changed to a nitric acid ion type exchange resin by using a 1 (mol/l) NaNO$_3$ aqueous solution, and the liberated chloride ions were titrated with a silver nitrate aqueous solution by using the potential-difference titration device (COMTITE-900, manufactured by Hiranuma Sangyo Co.) (A mols).

Next, the same ion-exchange membrane was immersed in a 1 (mol/l) NaCl aqueous solution for not less than 4 hours, and was washed with ion-exchanged water to a sufficient degree. The membrane was taken out, water on the surfaces thereof was wiped with a tissue paper or the like, and the weight (W g) thereof when wet was measured. Next, the membrane was dried at 60° C. for 5 hours under a reduced pressure, and the weight was measured (D g). Based on the above measured values, the ion-exchange capacity was found in compliance with the following formula, Ion-exchange capacity=$A$×1000/W[mmol/g-dry weight]

Water content=100×($W$–$D$)/$D$ [%]

Fixed ion concentration=ion-exchange capacity/water content×100[mmol/g-water]

(2) Membrane Resistance.

An ion-exchange membrane was held in a two-chamber cell equipped with a platinum black electrode, a 3 (mol/l) sulfuric acid aqueous solution was filled on both sides of the ion-exchange membrane, a resistance across the electrodes was measured relying on an AC bridge (frequency of 1000 cycles/sec) at 25° C., and the membrane resistance was found relying upon a difference between the resistance across the electrodes and the resistance across the electrodes of when the ion-exchange membrane was not set up. The membrane used for the measurement had been equilibrated in advance in a 3 (mol/l) sulfuric acid aqueous solution.

(3) Surface Roughness Rz.

The roughness of the surfaces of the ion-exchange membrane was measured by using a three-dimensional roughness measuring instrument (Model TDF-3A, manufactured by Kosaka Kenkyujo Co.). The length of evaluation was set to be 11 mm on an obtained curve, and a 10-point height of roughness profile (Rz) was regarded to be the surface roughness Ra of the ion-exchange membrane.

(4) Flexibility.

The ion-exchange membrane that was dried was placed in an atmosphere of a temperature of 25° C. and a relative humidity of 60% overnight or longer to adjust the wet degree. A sample was cut therefrom maintaining a width of 30 mm and a length of 20 cm and was measured for its Clark's stiffness degree in compliance with the JIS-P8143. The smaller the value, the more flexible the ion-exchange membrane.

(5) Burst Strength.

The ion-exchange membrane was immersed in a 1 mol/l HCl aqueous solution for not less than 4 hours and was washed with ion-exchanged water to a sufficient degree. Next, the ion-exchange membrane was measured for its burst strength by using the Mullen type burst strength tester (manufactured by Toyo Seiki Seisakusho Co.).

(6) Amount of Permeation of Medicine Through a Virtual Skin System.

Figure 2:
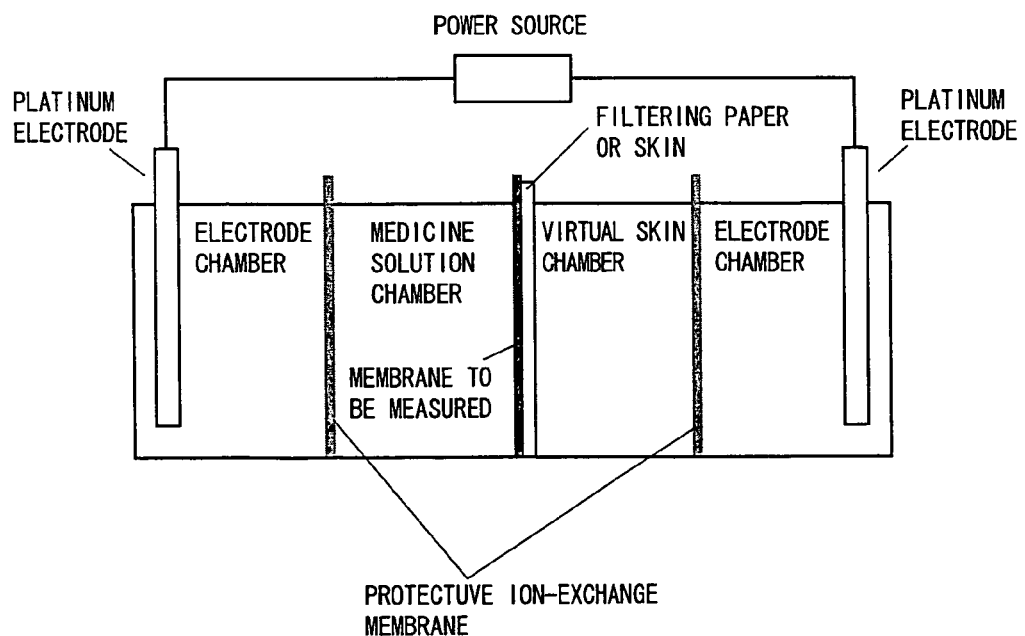
FIG. 2 is a view schematically illustrating a device used for measuring the amounts of permeation of the medicine according to the embodiment.

An aqueous solution containing 10% by weight of a polyvinyl alcohol (NH-20 manufactured by Nihon Gosei Co.) was applied onto a filtering paper (filtering paper 5C for chemical analysis manufactured by Advantech Co.) in such an amount that the applied amount of the polyvinyl alcohol after the solvent was removed was 2 mg/cm$^2$. Thereafter, the filtering paper was left to stand at room temperature for not shorter than 24 hours to remove water thereby to obtain a virtual skin. Next, the virtual skin, the ion-exchange membrane to be measured and protective ion-exchange membranes that prevent the medicine from arriving at the electrode, were set in a cell shown in FIG. 2, and the medicine solution chamber was filled with an aqueous solution of medicine of a predetermined concentration, a virtual skin chamber was filled with an aqueous solution of 0.9% by weight of sodium chloride, and the two electrode chambers were filled with a 0.1 (mol/l) sodium lactate aqueous solution. As the protective ion exchange membrane, there was used an anion-exchange membrane obtained in Preparation Example 1 that will be described later when the ion-exchange membrane to be measured was the cation-exchange membrane, and there was used a cation-exchange membrane obtained in Preparation Example 7 that will be described later when the object to be measured was the anion-exchange membrane. Next, an electric current was supplied for one hour at a predetermined constant current density or at a constant voltage while maintaining the cell at 25° C. and stirring the medicine solution chamber and the virtual skin chamber. After the end of supplying the electric current, the solution in the virtual skin chamber was readily drained and the amount of medicine was measured relying on a liquid chromatography. The same operation was executed without supplying the electric current to measure a blank value. A difference from the amount of medicine of when the current was supplied was calculated, and was regarded to be the amount the medicine has permeated.

(7) Amount of Permeation of Medicine Through a Living Body Skin System.

As living body skins, there were used a shaved skin of a back portion of a rabbit (male), a shaved skin of a back portion of a rat (six weeks old, male) and a shaved skin of a back portion of a micropig (five months old, female). The amounts the medicine has permeated through the living body skin systems were measured by the same method as the one for the virtual skin system.

Preparation Example 1

There was prepared a monomer composition comprising 380 g of a chloromethylstyrene, 20 g of a divinylbenzene and 20 g of a t-butylperoxyethyl hexanoate. 420 Grams of this monomer composition was introduced into a 500-ml glass container and in which a porous film (made of a polyethylene having a weight average molecular weight of 250,000, a thickness of 25 μm, an average pore size of 0.03 μm, percentage of voids of 37%) measuring 20 cm×20 cm was immersed under the atmospheric pressure at 25° C. for 10 minutes, so that the porous film was impregnated with the monomer composition. Next, the porous film was taken out from the monomer composition, covered on its both sides with polyester films of 100 μm thick, and was heated and polymerized under a nitrogen pressure of 3 kg/cm$^2$ at 80° C. for 5 hours. Thereafter, the obtained membrane was reacted in an aminating bath comprising 10 parts by mass of 30% by weight of a trimethylamine, 5 parts by mass of water and 5 parts by mass of acetone at room temperature for 5 hours to obtain a quaternary ammonium type anion-exchange membrane.

The obtained anion-exchange membrane was measured for its ion-exchange capacity, water content, fixed ion concentration, membrane resistance, membrane thickness, surface roughness, burst strength and flexibility. The results were as shown in Table 1.

Preparation Examples 2 to 5

Anion-exchange membranes were prepared in the same manner as in Preparation Example 1 but changing the monomer composition and the porous film into those of compositions shown in Table 1. Properties of the obtained membranes were as shown in Table 1.

Preparation Example 6

There was used a monomer composition shown in Table 1 and with which a porous film was impregnated in the same manner as in Preparation Example 1. The porous film was taken out from the monomer composition, covered on its both sides with polyester films of 100 μm thick, and was heated and polymerized under a nitrogen pressure of 3 kg/cm$^2$ at 45° C. for 3 hours and at 75° C. for 5 hours. Thereafter, the obtained membrane was immersed in a mixture of methyl iodide and n-hexane at a ratio of 1:3 (weight ratio) at 30° C. for 24 hours to obtain a quaternary pyridinium type anion-exchange membrane.

The obtained anion-exchange membrane was measured for its ion-exchange capacity, water content, fixed ion concentration, membrane resistance, membrane thickness, surface roughness, and flexibility. The results were as shown in Table 1.

Preparation Examples 7 and 8

Porous films were filled with monomer compositions shown in Table 1 in the same manner as in Preparation Example 1. Thereafter, the porous films were taken out from the monomer compositions, covered on their both sides with polyester films of 100 μm thick, and was heated and polymerized under a nitrogen pressure of 3 kg/cm$^2$ at 80° C. for 5 hours. Thereafter, the obtained membranes were immersed in a mixture of sulfuric acid of a concentration of 98% and chlorosulfonic acid of a purity of not lower than 90% at a ratio of 1:1 at 40° C. for 45 minutes to obtain sulfonic acid type cation-exchange membranes.

The obtained cation-exchange membranes were measured for their ion-exchange capacities, water contents, fixed ion concentrations, membrane resistances, membrane thicknesses, surface roughness, and flexibilities. The results were as shown in Table 1.

TABLE 1

| Preparation Example | Porous film | Composition (weight ratio) | | | | | Properties of ion-exchange membranes |
|---|---|---|---|---|---|---|---|
| | | CMS | 4-VP | St | DVB | PO | Ion-exchange group |
| 1 | A | 95 | 0 | 0 | 5 | 5 | quaternary ammonium type |
| 2 | A | 97.5 | 0 | 0 | 2.5 | 5 | quaternary ammonium type |
| 3 | A | 80 | 0 | 0 | 20 | 5 | quaternary ammonium type |
| 4 | B | 95 | 0 | 0 | 5 | 5 | quaternary ammonium type |
| 5 | C | 95 | 0 | 0 | 5 | 5 | quaternary ammonium type |
| 6 | A | 0 | 95 | 0 | 5 | 5 | quaternary pyridinium type |
| 7 | A | 0 | 0 | 90 | 10 | 5 | sulfonic acid type |
| 8 | A | 0 | 0 | 80 | 20 | 5 | sulfonic acid type |
| Neosepta AMX | woven fabric | | | | | | quaternary ammonium type |
| Neosepta CMX | woven fabric | | | | | | sulfonic acid type |

| | Properties of ion-exchange membranes | | | | | | | |
|---|---|---|---|---|---|---|---|---|
| Preparation Example | Ion-exchange capacity [mmonl/g-dry membrane] | Water content (%) | Fixed ion concentration [mmol/g-water] | Membrane resistance [Ω · cm$^2$] | Membrane thickness [μm] | Surface roughness [μm] | Burst strength [MPa] | Clark's stiffness [cm$^3$/100] |
| 1 | 1.8 | 22 | 8.2 | 0.08 | 32 | 1 or less | 0.37 | 1.8 |
| 2 | 2 | 35 | 5.7 | 0.07 | 32 | 1 or less | 0.35 | 1.2 |
| 3 | 1.6 | 12 | 13.3 | 0.32 | 30 | 1 or less | 0.37 | 2.8 |
| 4 | 1.9 | 24 | 7.9 | 0.06 | 20 | 1 or less | 0.25 | 0.6 |

TABLE 1-continued

| 5 | 1.8 | 23 | 7.8 | 0.22 | 90 | 1 | 0.18 | 10 |
| 6 | 1.9 | 23 | 8.3 | 0.08 | 31 | 1 or less | 0.37 | 1.8 |
| 7 | 2.4 | 29 | 8.3 | 0.08 | 31 | 1 or less | 0.38 | 2.2 |
| 8 | 2 | 18 | 11.1 | 0.17 | 29 | 1 or less | 0.4 | 3.2 |
| Neosepta AMX | 1.5 | 25 | 6.0 | 0.35 | 150 | 11 | 0.42 | 35 |
| Neosepta CMX | 1.6 | 28 | 5.7 | 0.36 | 160 | 12 | 0.45 | 41 |

Porous film
A: made of a polyethylene having a weight average molecular weight of 250,000, a thickness of 25 μm, an average pore size of 0.03 μm and a percentage of voids of 37%.
B: made of a polyethylene having a weight average molecular weight of 200,000, a thickness of 16 μm, an average pore size of 0.03 μm and a percentage of voids of 47%.
C: made of a polytetrafluoroethylene having a thickness of 80 μm, an average pore size of 1 μm and a percentage of voids of 80%.
CMS: chloromethylstyrene
4-VP: 4-vinylpyridine
St: styrene
DVB: divinylbenzene
PO: t-butylperoxyethyl hexanoate Examples 1 to 6

Amounts of permeation of the medicine were measured by using the virtual skin under the conditions of using a 10 mmol/l solution of an ascorbic acid phosphate magnesium salt which is an anionic medicine and a current density of 0.5 mA/cm² constant. Table 2 shows the ion-exchange membranes that were used and the amounts the medicine has permeated.

Comparative Example 1

The amount of permeation of the medicine through the virtual skin system was measured in the same manner as in Example 1 but using the Neosepta AMX (manufactured by Tokuyama Corp., membrane properties are as described in Table 1) which is an anion-exchange membrane as the ion-exchange membrane using, as the reinforcement, the woven fabric used in the conventional iontophoresis. The results were as shown in Table 2.

Comparative Example 2

The amount of permeation of the medicine was measured in the same manner as in Example 1 by using the virtual skin only but without using the ion-exchange membrane. The results were as shown in Table 2.

TABLE 2

| | Ion-exchange membrane | Medicine concen- tration [mmol/L] | Current density [mA/cm²] | Amount of permeation [μmol/cm²] |
| --- | --- | --- | --- | --- |
| Example 1 | membrane of preparation Example 1 | 10 | 0.5 | 7.4 |
| Example 2 | membrane of preparation Example 2 | 10 | 0.5 | 3.5 |
| Example 3 | membrane of preparation Example 3 | 10 | 0.5 | 6.8 |
| Example 4 | membrane of preparation Example 4 | 10 | 0.5 | 6.6 |
| Example 5 | membrane of preparation Example 5 | 10 | 0.5 | 7.2 |

TABLE 2-continued

| | Ion-exchange membrane | Medicine concen- tration [mmol/L] | Current density [mA/cm²] | Amount of permeation [μmol/cm²] |
| --- | --- | --- | --- | --- |
| Example 6 | membrane of preparation Example 6 | 10 | 0.5 | 7.0 |
| Comparative Example 1 | Neosepta AMX | 10 | 0.5 | 1.0 |
| Comparative Example 2 | none | 10 | 0.5 | 0.2 |

Used medicine: ascorbic acid phosphate magnesium salt

Example 7

The amount of permeation of the medicine was measured by using the virtual skin system obtained in Preparation Example 1 under the conditions of using a 1 mmol/l solution of a dexamethasone phosphate disodium salt instead of using the 10 mmol/l solution of the ascorbic acid phosphate magnesium salt and a current density of 0.05 mA/cm² constant. The results were as shown in Table 3.

Comparative Example 3

The amount of permeation of the medicine through the virtual skin system was measured in the same manner as in Example 7 but using the Neosepta AMX (manufactured by Tokuyama Corp., membrane properties are as described in Table 1) which is an anion-exchange membrane as the ion-exchange membrane using, as the reinforcement, the woven fabric used in the conventional iontophoresis. The results were as shown in Table 3.

Comparative Example 4

The amount of permeation of the medicine was measured in the same manner as in Example 7 by using the virtual skin only but without using the ion-exchange membrane. The results were as shown in Table 3.

TABLE 3

| Example No. | Medicine concentration [mmol/L] | Current density [mA/cm$^2$] | Amount of permeation [μmol/cm$^2$] |
|---|---|---|---|
| Ex. 7 | 1 | 0.05 | 0.07 |
| Comp. Ex. 3 | 1 | 0.05 | not detected |
| Comp. Ex. 4 | 1 | 0.05 | not detected |

Used medicine: dexamethasone phosphate disodium salt

Examples 8, 9 and Comparative Examples 5, 6

Amounts of permeation of the medicine were measured by using the virtual skin under the conditions of using a 10 mmol/l solution of a histamine dihydrochloride which is a cationic medicine and a current density of 0.5 mA/cm$^2$ constant. Table 4 shows the ion-exchange membranes that were used and the amounts the medicine has permeated.

TABLE 4

| Example No. | Ion-exchange membrane | Medicine concentration [mmol/L] | Current density [mA/cm$^2$] | Amount of permeation [μmol/cm$^2$] |
|---|---|---|---|---|
| Ex. 8 | membrane of preparation Example 7 | 10 | 0.5 | 5.0 |
| Ex. 9 | membrane of preparation Example 8 | 10 | 0.5 | 5.5 |
| Comp. Ex. 5 | Neosepta CMX | 10 | 0.5 | 2.0 |
| Comp. Ex. 6 | none | 10 | 0.5 | 1.2 |

Used medicine: histamine dihydrochloride

Example 10, Comparative Examples 7, 8

Amounts of permeation of the medicine were measured by using the virtual skin under the conditions of using a 10 mmol/l solution of a lidocaine hydrochloride which is a cationic medicine and a current density of 0.5 mA/cm$^2$ constant. Table 5 shows the ion-exchange membranes that were used and the amounts the medicine has permeated.

TABLE 5

| Example No. | Ion-exchange membrane | Medicine concentration [mmol/L] | Current density [mA/cm$^2$] | Amount of permeation [μmol/cm$^2$] |
|---|---|---|---|---|
| Ex. 10 | membrane of preparation Example 7 | 10 | 0.5 | 2.5 |
| Comp. Ex. 7 | Neosepta CMX | 10 | 0.5 | 1.5 |
| Comp. Ex. 8 | none | 10 | 0.5 | 0.1 |

Used medicine: lidocaine hydrochloride

Examples 11, 12, Comparative Example 9

Amounts of permeation of the medicine were measured by using the virtual skin system under the conditions of using a 10 mmol/l solution of a sodium ascorbate which is an anionic medicine and applying a constant voltage of 10 V. Table 6 shows the ion-exchange membranes that were used and the amounts the medicine has permeated.

TABLE 6

| Example No. | Ion-exchange membrane | Medicine concentration [mmol/L] | Current density [mA/cm$^2$] | Amount of permeation [μmol/cm$^2$] |
|---|---|---|---|---|
| Ex. 11 | membrane of preparation Example 1 | 10 | 10 | 5.6 |
| Ex. 12 | membrane of preparation Example 5 | 10 | 10 | 2.8 |
| Comp. Ex. 9 | Neosepta AMX | 10 | 10 | 0.2 |

Used medicine: sodium ascorbate

Example 13, Comparative Example 10

Amounts of permeation of the medicine were measured by using a living body skin system under the conditions of using a 10 mmol/l solution of an ascorbic acid phosphate magnesium salt and a current density of 0.5 mA/cm$^2$ constant. The living body skin was the shaved skin of a rat (male). Table 7 shows the ion-exchange membranes that were used and the amounts the medicine has permeated.

TABLE 7

| Ex. No. | Ion-exchange membrane | Living body skin | Medicine concentration [mmol/L] | Current density [mA/cm$^2$] | Amount of permeation [μmol/cm$^2$] |
|---|---|---|---|---|---|
| Ex. 13 | membrane of preparation Example 1 | rat | 10 | 0.5 | 0.6 |
| Comp. Ex. 10 | Neosepta AMX | rat | 10 | 0.5 | 0.35 |

Used medicine: ascorbic acid phosphate magnesium salt

Example 14, Comparative Example 11

Amounts of permeation of the medicine were measured by using a living body skin system under the conditions of using a 10 mmol/l solution of a histamine dihydrochloride and a current density of 0.5 mA/cm$^2$ constant. The living body skin was the shaved skin of a rabbit (male). Table 8 shows the ion-exchange membranes that were used and the amounts the medicine has permeated.

TABLE 8

| Ex. No. | Ion-exchange membrane | Living body skin | Medicine concentration [mmol/L] | Current density [mA/cm$^2$] | Amount of permeation [μmol/cm$^2$] |
|---|---|---|---|---|---|
| Ex. 14 | membrane of preparation Example 7 | rabbit | 10 | 0.5 | 1.6 |
| Comp. Ex. 11 | Neosepta CMX | rabbit | 10 | 0.5 | 1 |

Used medicine: histamine dihydrochloride

Example 15, Comparative Example 12

Amounts of permeation of the medicine were measured by using a living body skin system under the conditions of using a 10 mmol/l solution of an ascorbic acid phosphate magnesium salt and applying a constant voltage of 15 V. The living body skin was the shaved skin of a rat (male). Table 9 shows the ion-exchange membranes that were used and the amounts the medicine has permeated.

TABLE 9

| Ex. No. | Ion-exchange membrane | Living body skin | Medicine concentration [mmol/L] | Current density [mA/cm$^2$] | Amount of permeation [μmol/cm$^2$] |
|---|---|---|---|---|---|
| Ex. 15 | membrane of preparation Example 1 | rat | 10 | 15 | 0.65 |
| Comp. Ex. 12 | Neosepta AMX | rat | 10 | 15 | 0.25 |

Used medicine: ascorbic acid phosphate magnesium salt

Example 16, Comparative Example 13

Amounts of permeation of the medicine through the living body skin system was measured in the same manner as in Example 13 but using, as the living body skin, the skin of the back portion of a micropig (Yucatan Micropic, 5 months old, female). Table 10 shows the ion-exchange membranes that were used and the amounts the medicine has permeated.

TABLE 10

| Ex. No. | Ion-exchange membrane | Living body skin | Medicine concentration [mmol/L] | Current density [mA/cm$^2$] | Amount of permeation [μmol/cm$^2$] |
|---|---|---|---|---|---|
| Ex. 16 | membrane of preparation Example 1 | micropig | 10 | 0.5 | 0.35 |
| Comp. Ex. 13 | Neosepta AMX | micropig | 10 | 0.5 | 0.2 |

Used medicine: ascorbic acid phosphate magnesium salt

The iontophoresis device of the present invention which employs an ion-exchange membrane using a porous film as the reinforcement makes it possible to administer the medicine in amounts greater than those accomplished by using the conventional ion-exchange membranes used in the iontophoresis.

The ion-exchange membrane for iontophoresis of the present invention exhibits flexibility yet maintaining the required strength, and excellently follows ruggedness, expansion, contraction and bending of the skin. By using a porous film as the reinforcement, further, a thin membrane is obtained yet maintaining a large strength probably due to the resin filled in relatively small amounts in the reinforcement. Further, the ion-exchange membrane of the invention exhibits a very small resistance due to its small thickness. When a cell is used as a power source, therefore, the medicine is administered in particularly large amounts. From the above points of view, the iontophoresis device using the ion-exchange membrane of the present invention is particularly useful when it is fabricated in a portable form.

Therefore, the iontophoresis device of the present invention exhibits excellent effect in all applications where use of the iontophoresis was so far considered, such as for beauty purpose, medical purpose and for health purpose by administering supplements. Besides, the iontophoresis device can be realized in a portable size offering a very high degree of practicability in wide applications.

The invention claimed is:

1. An iontophoresis device comprising (A) a working electrode assembly having a working electrode, a medicine-containing portion and an ion-exchange membrane, (B) a counter electrode assembly having an electrode which opposes said working electrode, and (C) a power source unit electrically connected to the working electrode assembly and to the counter electrode assembly, enabling an ionic medicine contained in said medicine containing portion to be permeated into a living body by electrophoresis through the ion-exchange membrane,
    wherein:
        said ion-exchange membrane has a structure in which voids of a porous film are filled with an ion-exchange resin;
        the ion-exchange membrane enables permeation of ions having the same polarity as that of the ionic medicine;
        the porous film comprises a polyolefin resin; and
        the voids in the porous film pierce through from the front surface to the back surface of the film.

2. An iontophoresis device according to claim 1, wherein said porous film has an average void size of 0.005 to 5.0 μm and a percentage of voids of 20 to 95%.

3. An iontophoresis device according to claim 1, wherein the ion-exchange membrane has a thickness of 5 to 150 μm.

4. An iontophoresis device according to claim 1, wherein the ion-exchange membrane contains the ion-exchange resin in an amount of 5 to 95% by weight.

* * * * *